United States Patent [19]

Van Well

[11] Plant 4,370

[45] Jan. 23, 1979

[54] COMPACT PEACH TREE

[75] Inventor: Peter J. Van Well, Wenatchee, Wash.

[73] Assignee: Van Well Nursery, Wenatchee, Wash.

[21] Appl. No.: 862,741

[22] Filed: Dec. 21, 1977

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Christensen, O'Connor, Johnson & Kindness

[57] ABSTRACT

A compact, semi-dwarf peach tree, this new variety is also characterized in its development of more fruit buds per lineal foot than with the Gold Medal tree.

2 Drawing Figures

BACKGROUND OF DISCOVERY

The invention or discovery relates to a new and distinct variety of peach tree apparently originating as a sport discovered in the form of a whole tree growing in an orchard of Gold Medal trees near the mouth of Moses Coulee in Douglas County, Wash.

DESCRIPTION OF THE ILLUSTRATIONS

The accompanying illustrations show the distinctly different growth habits and limb structures of my new variety compared with its parent, Gold Medal.

DESCRIPTION OF NEW VARIETY

Figures 1, 2:
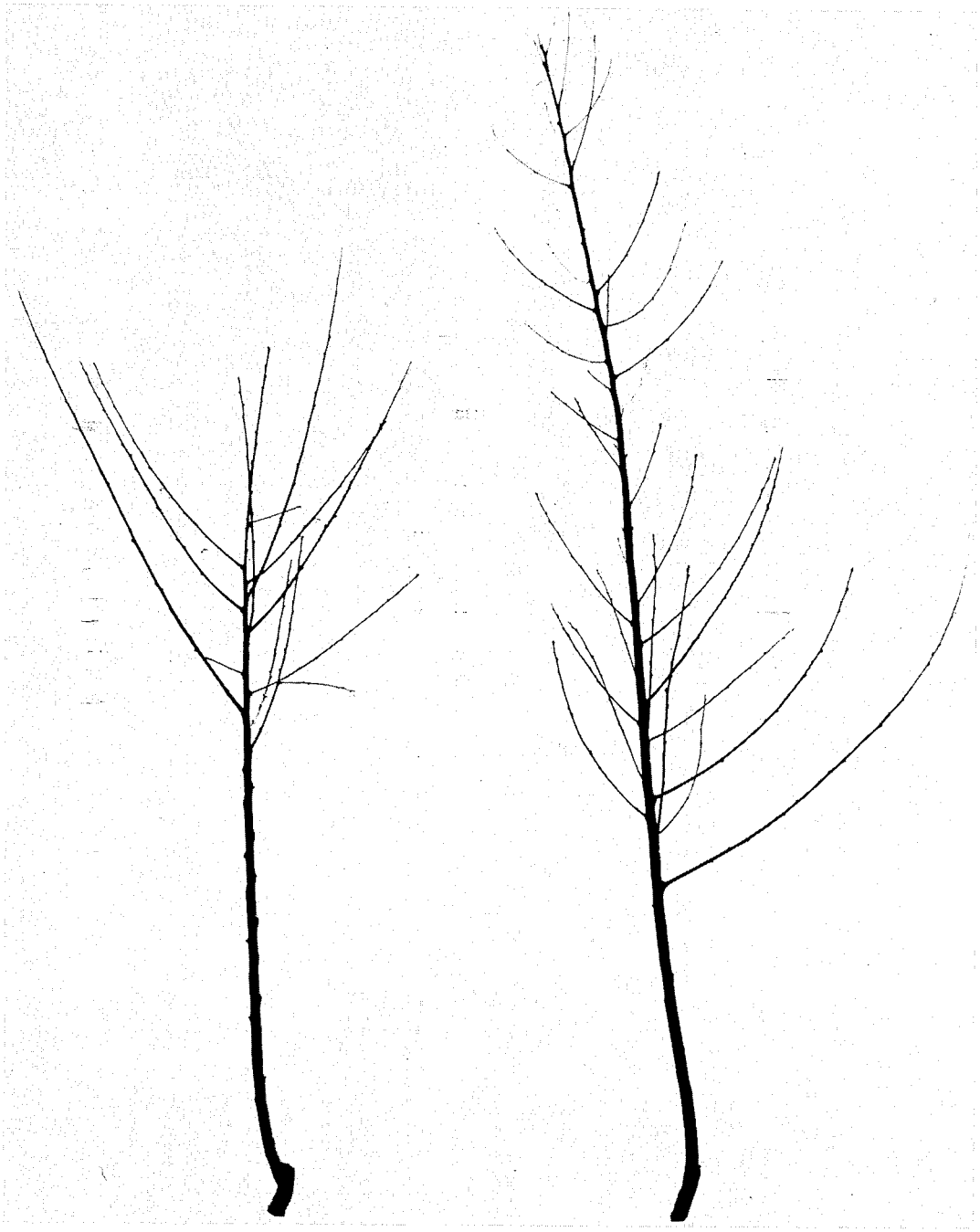
FIG. 1 is a photograph of a typical one-year old tree of my new variety.
FIG. 2 is a photograph of a typical one-year old tree of standard Gold Medal, both produced from buds set on similar root stock and allowed to develop under the same growing conditions.

The new variety has a compact semi-dwarf structure not found in the nearest similar variety, namely the standard Gold Medal variety. The improved tree also differs from Gold Medal in the development of more fruit buds per lineal foot and in the more vigorous growth and fruit bearing capabilities of the lateral buds along most of the terminal shoots. The growth of these lateral buds is such, particularly near the bases of the terminal shoots, that the base diameters of most such lateral buds range from one-half to three-fourths that of the base of the terminal shoots from which they branch. Also, the growth extensions of these lateral buds most often range from one-half to three-fourths the growth extension of the supporting terminal shoot itself and occasionally equal the length of the terminal shoot. In contrast, growth of the lateral buds near the base of the terminal shoot growth of standard Gold Medal are often sparse and small. Thus the growth characteristics of this new variety permits the maintenance of more fruiting wood on the lower branches of the tree.

Further identifying characteristics of my new variety are: Tree, medium small; semi-dwarf; moderately vigorous compact form. Flowers, leaves and fruit substantially identical to standard Gold Medal. Fruit, similar in size, shape and matures the same time as Gold Medal. Color is identical to Gold Medal.

Another peach tree variety with which my distinct new variety may be compared is that of U.S. Plant Pat. No. 3,217, Pratt Strain Compact Redhaven. While the tree structure and vegetative growth of my new variety is very similar to that of said U.S. Plant Pat. No. 3,217, the fruit of my new variety matures approximately twenty days later, is smaller and does not color with the full red blush typical of the variety, Redhaven.

Subsequent to my discovery of the new variety, I reproduced it by budding through two successive generations at my orchard located on Grant Road, East Wenatchee, Douglas County, Wash. Each successive generation has all of the characteristics of the original sport or mutation, so that the characteristics of my new variety appear to be stable.

Having thus disclosed my improved variety, I claim:

1. A new and distinct variety of peach tree characterized as to novelty by its compact, semi-dwarf habit of growth, by the development of more fruit buds than are normally found on trees of the standard Gold Medal variety, and by the more vigorous growth and fruit bearing capabilities of its lateral buds along most of its terminal shoots.

* * * * *